United States Patent
Dehghan Marvast et al.

(10) Patent No.: US 10,327,724 B2
(45) Date of Patent: Jun. 25, 2019

(54) DETECTION AND CHARACTERIZATION OF AORTIC PATHOLOGIES

(71) Applicant: INTERNATIONAL BUSINESS MACHINES CORPORATION, Armonk, NY (US)

(72) Inventors: Ehsan Dehghan Marvast, Palo Alto, CA (US); Tanveer F. Syeda-Mahmood, Cupertino, CA (US); Hongzhi Wang, Santa Clara, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/728,546

(22) Filed: Oct. 10, 2017

(65) Prior Publication Data
US 2019/0105008 A1   Apr. 11, 2019

(51) Int. Cl.
*G06K 9/00* (2006.01)
*A61B 6/00* (2006.01)
(Continued)

(52) U.S. Cl.
CPC .......... *A61B 6/5217* (2013.01); *A61B 6/03* (2013.01); *A61B 6/504* (2013.01); *G06F 16/51* (2019.01);
(Continued)

(58) Field of Classification Search
CPC ......... A61B 6/5217; A61B 6/03; A61B 6/504; G06T 7/62; G06F 17/30256; G06F 17/3028
See application file for complete search history.

(56) References Cited

U.S. PATENT DOCUMENTS

| 7,486,811 B2 * | 2/2009 | Kaufman | G06T 7/0012 378/21 |
| 7,567,696 B2 * | 7/2009 | Moreau-Gobard | G06T 7/12 382/131 |

(Continued)

OTHER PUBLICATIONS

Lu et al., "Diagnostic value of multislice computerized tomography angiography for aortic dissection: A comparison with DSA", Experimental and Therapeutic Medicine 13: 405-412, 2017, Received May 30, 2016; Accepted Aug. 18, 2016.

(Continued)

*Primary Examiner* — Gregory M Desire
(74) *Attorney, Agent, or Firm* — L. Jeffrey Kelly; Douglas M. Crockatt (57) ABSTRACT

According to one or more embodiments, a method, a computer program product, and a computer system for detecting and characterizing aortic pathologies are provided. The method may include receiving, by a computer, one or more tomograph scan images corresponding to a patient's aorta. The one or more received tomograph scan images may be analyzed by the computer for one or more image features associated with one or more aortic pathologies, such as aortic dissection or an aortic aneurysm. One or more image features associated with the one or more aortic pathologies may be identified in the one or more analyzed tomograph scan images, which may allow the determination of an aortic pathology associated with the patient's aorta based on the identification of the image features. A portion of the aorta and one or more branch arteries corresponding to the determined aortic pathology may then be identified.

20 Claims, 7 Drawing Sheets

(51) Int. Cl.

| | | |
|---|---|---|
| *A61B 6/03* | (2006.01) | |
| *G06T 7/00* | (2017.01) | |
| *G06T 7/62* | (2017.01) | |
| *G06F 16/51* | (2019.01) | |
| *G06F 16/583* | (2019.01) | |
| *G06F 19/00* | (2018.01) | |

(52) U.S. Cl.
CPC ........ *G06F 16/5838* (2019.01); *G06T 7/0014* (2013.01); *G06T 7/62* (2017.01); *G06F 19/321* (2013.01); *G06F 19/325* (2013.01); *G06T 2207/10072* (2013.01); *G06T 2207/30101* (2013.01); *G06T 2207/30204* (2013.01)

(56) References Cited

U.S. PATENT DOCUMENTS

| | | | | |
|---|---|---|---|---|
| 7,873,194 | B2* | 1/2011 | Begelman | A61B 5/02007 |
| | | | | 345/418 |
| 8,983,570 | B2* | 3/2015 | Stegmann | G01N 33/74 |
| | | | | 600/300 |
| 9,060,960 | B2* | 6/2015 | Granville | A61K 31/00 |
| 2008/0101674 | A1 | 5/2008 | Begelman et al. | |
| 2010/0309198 | A1* | 12/2010 | Kauffmann | A61B 6/504 |
| | | | | 345/419 |
| 2011/0206257 | A1* | 8/2011 | Qanadli | A61B 5/02014 |
| | | | | 382/130 |
| 2012/0239131 | A1* | 9/2012 | Sulaimon | A61L 31/16 |
| | | | | 623/1.13 |
| 2013/0066197 | A1* | 3/2013 | Pruvot | G06T 7/0012 |
| | | | | 600/427 |
| 2015/0227695 | A1* | 8/2015 | Becker | G06F 19/321 |
| | | | | 705/3 |
| 2016/0300026 | A1 | 10/2016 | Bogoni et al. | |

OTHER PUBLICATIONS

Wang et al., "Finding a Path for Segmentation Through Sequential Learning", IPMI 2015, LNCS 9123, pp. 488-500.

Mell et al., "The NIST Definition of Cloud Computing", Recommendations of the National Institute of Standards and Technology, Special Publication 800-145, U.S. Department of Commerce, Sep. 2011, 7 pages.

Wang et al., "Multi-Atlas Segmentation with Joint Label Fusion", IEEE Trans Pattern Anal Mach Intell. Mar. 2013; 35 (3): 611-623, Published online Jun. 26, 2012 doi: 10.1109/TPAMI.2012.143.

* cited by examiner

DETECTION AND CHARACTERIZATION OF AORTIC PATHOLOGIES

BACKGROUND

The present invention relates generally to field of medicine, and more particularly to detection and characterization of aortic pathologies, such as aortic aneurysms and aortic dissection.

The aorta is the largest artery within the human body. It originates from the left ventricle and distributes oxygenated blood to all other parts of the body. The aorta can be divided into two main regions: the thoracic aorta and the abdominal aorta. The thoracic aorta may be further subdivided into three main sections: the ascending aorta, the aortic arch, and the descending aorta. The various regions and sections of the aorta may present with, among other things, one or more pathologies, such as aortic dissection or an aortic aneurysm. An aortic dissection may occur when a tear inside the intimal wall of an artery allows blood to flow between the two layers of the vessel wall. In addition to the aorta, the iliac, renal and carotid arteries can also be affected. An aortic aneurysm may occur when the aorta dilates, which may cause a thinning of the wall of the aorta. Both aortic dissections and aortic aneurysms may cause, among other things, ischemia or aortic rupture, which may pose a life-threatening medical emergency.

SUMMARY

Embodiments of the present invention disclose a method, system, and computer program product for detecting and characterizing aortic pathologies. According to one embodiment, a method for detecting and characterizing aortic pathologies is provided. The method may include receiving, by a computer, one or more tomograph scan images corresponding to a patient's aorta. The one or more received tomograph scan images may be analyzed by the computer for one or more image features associated with one or more aortic pathologies, such as aortic dissection or an aortic aneurysm. One or more image features associated with the one or more aortic pathologies may be identified in the one or more analyzed tomograph scan images, which may allow the determination of an aortic pathology associated with the patient's aorta based on the identification of the image features. A portion of the aorta and one or more branch arteries corresponding to the determined aortic pathology may then be identified.

According to another embodiment, a computer system for detecting and characterizing aortic pathologies is provided. The computer system may include one or more processors, one or more computer-readable memories, one or more computer-readable tangible storage devices, and program instructions stored on at least one of the one or more storage devices for execution by at least one of the one or more processors via at least one of the one or more memories, whereby the computer system is capable of performing a method. The method may include receiving, by a computer, one or more tomograph scan images corresponding to a patient's aorta. The one or more received tomograph scan images may be analyzed by the computer for one or more image features associated with one or more aortic pathologies, such as aortic dissection or an aortic aneurysm. One or more image features associated with the one or more aortic pathologies may be identified in the one or more analyzed tomograph scan images, which may allow the determination of an aortic pathology associated with the patient's aorta based on the identification of the image features. A portion of the aorta and one or more branch arteries corresponding to the determined aortic pathology may then be identified.

According to yet another embodiment, a computer program product for detecting and characterizing aortic pathologies is provided. The computer program product may include one or more computer-readable storage devices and program instructions stored on at least one of the one or more tangible storage devices, the program instructions executable by a processor. The program instructions are executable by a processor for performing a method that may accordingly include receiving, by a computer, one or more tomograph scan images corresponding to a patient's aorta. The one or more received tomograph scan images may be analyzed by the computer for one or more image features associated with one or more aortic pathologies, such as aortic dissection or an aortic aneurysm. One or more image features associated with the one or more aortic pathologies may be identified in the one or more analyzed tomograph scan images, which may allow the determination of an aortic pathology associated with the patient's aorta based on the identification of the image features. A portion of the aorta and one or more branch arteries corresponding to the determined aortic pathology may then be identified.

BRIEF DESCRIPTION OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

Embodiments of the present invention relate generally to the field of medicine, and more particularly to detection and characterization of aortic pathologies, such as aortic aneurysms and aortic dissection. The following described exemplary embodiments provide a system, method and program product to, among other things, determine one or more aortic pathologies affecting a patient. Therefore, embodiments of the present invention have the capacity to improve the field of medicine by allowing enhanced diagnosis of aortic and other arterial and venous pathologies by automatically characterizing their severity and extent. For example, a patient may present with a dilated ascending aorta having a diameter larger than approximately six millimeters. Thus, the computer-implement method, computer system, and computer program product disclosed herein may, among other things, be used to diagnose aortic pathologies in order to allow optimal and rapid treatment. Furthermore, while the method, system, and computer program product disclosed herein are described with respect to aortic pathologies, the described embodiments may also be configured for the detection and characterization of pathologies of other blood vessels, such as veins and other arteries.

As previously described, the aorta is the largest artery within the human body. The various regions and sections of the aorta may present with, among other things, one or more pathologies, such as aortic dissection or an aortic aneurysm, that are serious, life-threatening medical emergencies. Often, a diagnosis of aneurysm or dissection of a vessel may be made by visualization of the vessel in a contrast-enhanced computer tomography (CE-CT) scan of the chest and/or abdomen. Other imaging modalities such as transesophageal echocardiogram and MRI can also be used. An aortic dissection can be characterized by factors such as type, determined by the position of a false lumen, and also extension of the dissection to other vessels branching off the main vessel (i.e. renal, iliac and carotid arteries in an aortic dissection). The dissection type, its extent and some other clinical indications and contraindications are the deciding factors in the selection of the treatment. It may, therefore, be advantageous to enhance detection and characterization of such aortic pathologies in order to diagnose and treat such pathologies quickly and effectively. Accordingly, the invention disclosed herein may improve the field of computing by providing a system, method, and program product to detect, characterize, and suggest treatment for aortic pathologies without user intervention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The following described exemplary embodiments provide a system, method and program product that detects and characterizes one or more aortic pathologies in patients. According to the present embodiment, this detection and characterization may be provided through analysis of one or more tomograph scan images to detect one or more image features associated with the aortic pathologies. Based on the detection of the image features, the appropriate aortic pathology may be diagnosed and treated.

Figure 1:
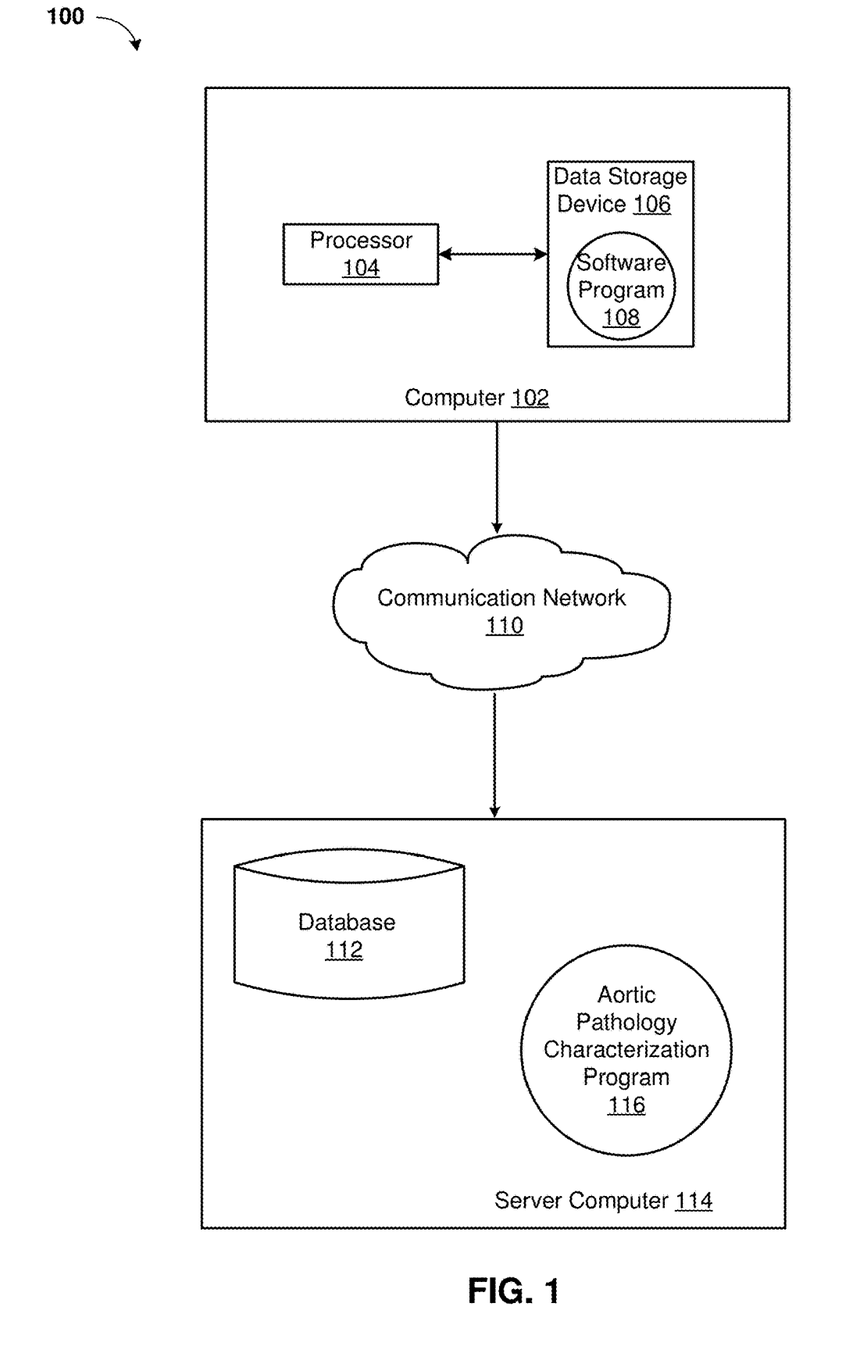
FIG. 1 illustrates a networked computer environment according to at least one embodiment.

Referring now to FIG. 1, a functional block diagram illustrating an aortic pathology characterization system 100 (hereinafter "system") for improved detection and characterization of aortic pathologies, such as aortic aneurysms and aortic dissection, is shown. It should be appreciated that FIG. 1 provides only an illustration of one implementation and does not imply any limitations with regard to the environments in which different embodiments may be implemented. Many modifications to the depicted environments may be made based on design and implementation requirements.

The system 100 may include a computer 102 and a server computer 114. The computer 102 may communicate with the server computer 114 via a communication network 110 (hereinafter "network"). The computer 102 may include a software program 108 that is stored on a data storage device 106 and is enabled to interface with a user and communicate with the server computer 114. As will be discussed below with reference to FIG. 5 the computer 102 may include internal components 800A and external components 900A, respectively, and the server computer 114 may include internal components 800B and external components 900B, respectively. The computer 102 may be, for example, a mobile device, a telephone, a personal digital assistant, a netbook, a laptop computer, a tablet computer, a desktop computer, or any type of computing devices capable of running a program, accessing a network, and accessing a database.

The server computer 114 may also operate in a cloud computing service model, such as Software as a Service (SaaS), Platform as a Service (PaaS), or Infrastructure as a Service (IaaS), as discussed below. The server computer 114 may also be located in a cloud computing deployment model, such as a private cloud, community cloud, public cloud, or hybrid cloud. The server computer 114, which may be used for detecting and characterizing aortic pathologies, notifying users of the aortic pathologies, and determining optimal treatment options is enabled to run an Aortic Pathology Characterization Program 116 (hereinafter "program") that may interact with a database 112. The Aortic Pathology Characterization Program method is explained in more detail below with respect to FIG. 4. In one embodiment, the computer 102 may operate as an input device including a user interface while the program 116 may run primarily on server computer 114. In an alternative embodiment, the program 116 may run primarily on one or more computers 102 while the server computer 114 may be used for processing and storage of data used by the program 116. It should be noted that the program 116 may be a standalone program or may be integrated into a larger aortic pathology characterization program.

It should be noted, however, that processing for the program 116 may, in some instances be shared amongst the computers 102 and the server computers 114 in any ratio. In another embodiment, the program 116 may operate on more than one computer, server computer, or some combination of computers and server computers, for example, a plurality of computers 102 communicating across the network 110 with a single server computer 114. In another embodiment, for example, the program 116 may operate on a plurality of server computers 114 communicating across the network 110 with a plurality of client computers. Alternatively, the program may operate on a network server communicating across the network with a mail server and a plurality of client computers.

The network 110 may include wired connections, wireless connections, fiber optic connections, or some combination thereof. In general, the network 110 can be any combination of connections and protocols that will support communications between the computer 102 and the server computer 114. The network 110 may include various types of networks, such as, for example, a local area network (LAN), a wide area network (WAN) such as the Internet, a telecommunication network, a wireless network, a public switched network and/or a satellite network.

Figure 2:
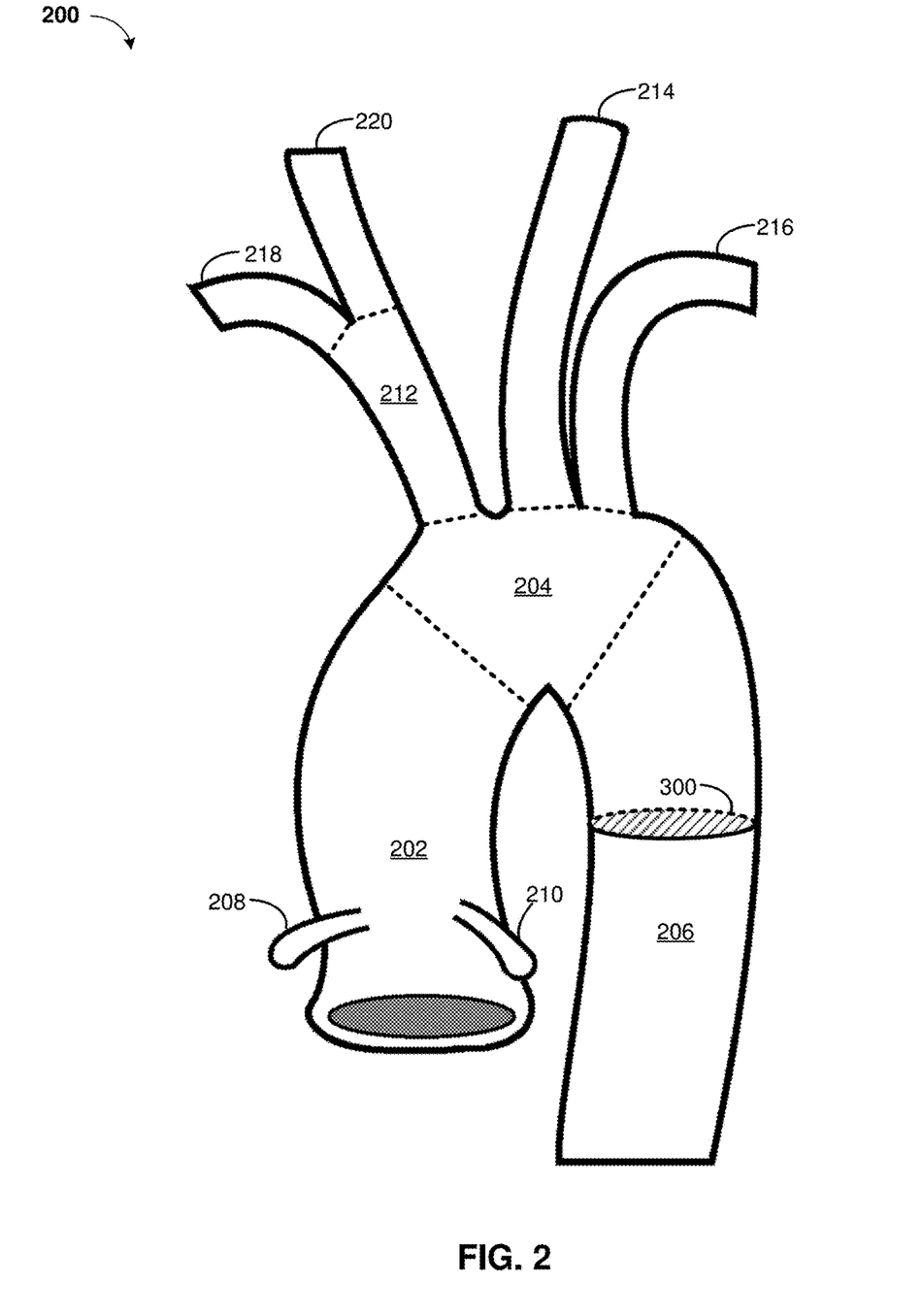
FIG. 2 depicts an illustration of a thoracic aorta according to at least one embodiment.

Referring to FIG. 2, an illustration of a thoracic aorta 200 is depicted. The thoracic aorta 200 includes an ascending aorta 202, an aortic arch 204, and a descending aorta 206. The right coronary artery 208 and left coronary artery 210 branch off of the ascending aorta 202 just above the aortic root. The brachiocephalic artery 212, the left common carotid artery 214, and the left subclavian artery 216 each branch off of the aortic arch 204. The brachiocephalic artery 212 is, in turn, connected to the right subclavian artery 218 and the right common carotid artery 220. The abdominal aorta is inferior and distal to the descending aorta 206 and is not depicted. One or more arteries, such as the hepatic, mesenteric, and left and right renal arteries, may branch off of the abdominal aorta. A tomograph scan 300 may be acquired from any part of the aorta. It may be appreciated that while the tomograph scan image 300 depicted in FIG. 2 corresponds to a cross section of the descending aorta, the tomograph scan image 300 may also correspond to respective cross sections of the ascending aorta, aortic arch, and abdominal aorta.

Figure 3A:
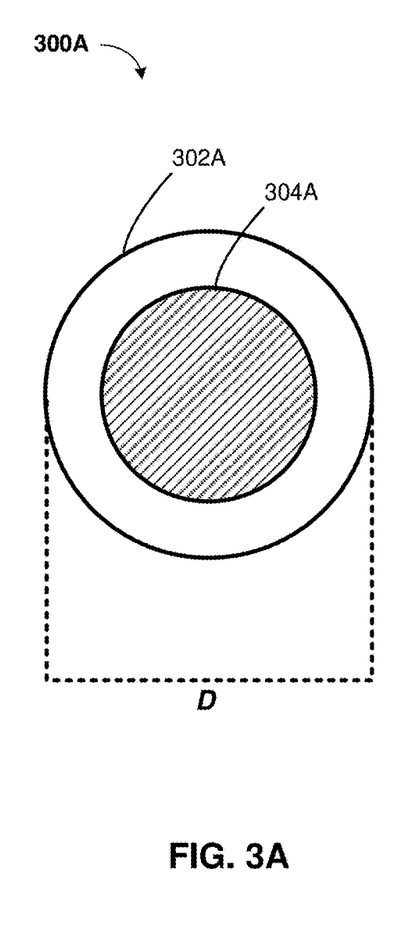
FIG. 3A is an exemplary tomograph scan image depicting a normal aorta to be analyzed by the computer system depicted in FIG. 1, according to at least one embodiment.
Figure 3B:
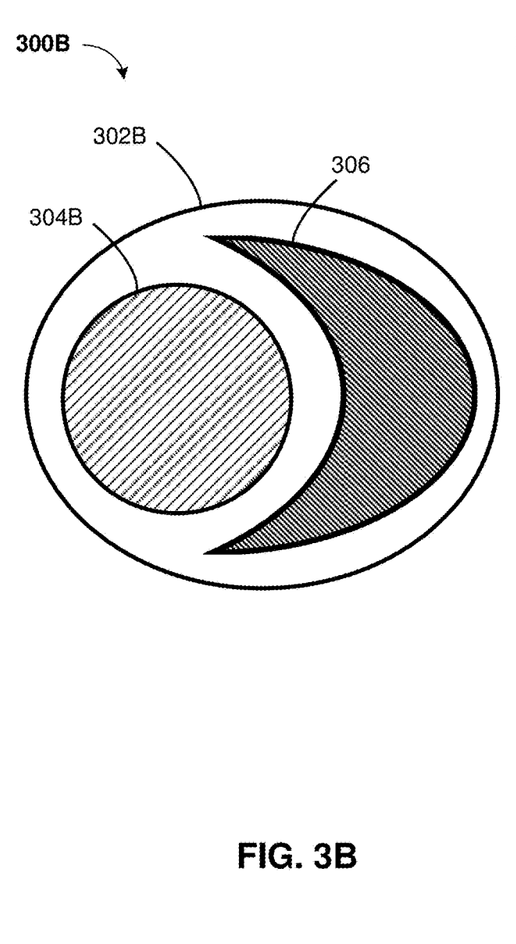
FIG. 3B is an exemplary tomograph scan image depicting an aortic dissection to be analyzed by the computer system depicted in FIG. 1, according to at least one embodiment.
Figure 3C:
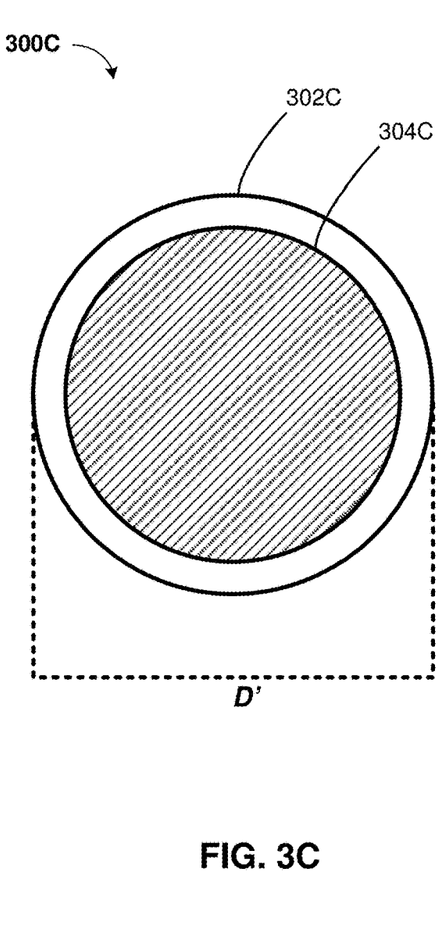
FIG. 3C is an exemplary tomograph scan image depicting an aortic aneurysm to be analyzed by the computer system depicted in FIG. 1, according to at least one embodiment.

With regard to FIGS. 3A-3C, one or more tomograph scan images of the aorta 200 that may be analyzed by the computer system 100 are depicted according to one embodiment. It may be appreciated that, by way of example and not of limitation, the tomograph scan images are cross-sectional images of the descending thoracic aorta. However, the one or more tomograph scan images may depict any portion of the thoracic and/or abdominal aorta, such as, for example, the aortic root, the ascending aorta, or the aortic arch.

Referring now to FIG. 3A, an exemplary tomograph scan image 300A depicting a cross-sectional view of a normal aorta, not having any diagnosable pathologies, to be analyzed by the computer system 100 depicted in FIG. 1 according to one embodiment is depicted. Tomograph scan image 300A may show an aorta 200 having a vascular wall 302A, a lumen 304A, and a diameter D.

Referring now to FIG. 3B, an exemplary tomograph scan image 300B of a cross-sectional view of an aortic dissection to be analyzed by the computer system 100 of FIG. 1, according to one embodiment, is depicted. Tomograph scan image 300B may show, among other things, an aorta having a vascular wall 302B, a lumen 304B, and a false lumen 306. It may be appreciated that the tomograph scan image 300B may depict both Stanford Type A and Type B aortic dissections.

Referring now to FIG. 3C is an exemplary tomograph scan image depicting a cross-sectional view of an aortic aneurysm to be analyzed by the computer system 100 depicted in FIG. 1, according to one embodiment. Tomograph scan image 300C may show an aorta having a vascular wall 302C, a lumen 304C, and a diameter D'. Diameter D' may be approximately 1.5 times the size of diameter D or greater. It may be appreciated that the tomograph scan image 300C may also show any type of aortic aneurysm, such as fusiform aneurysms, saccular aneurysms and pseudo-aneurysms.

Figure 4:
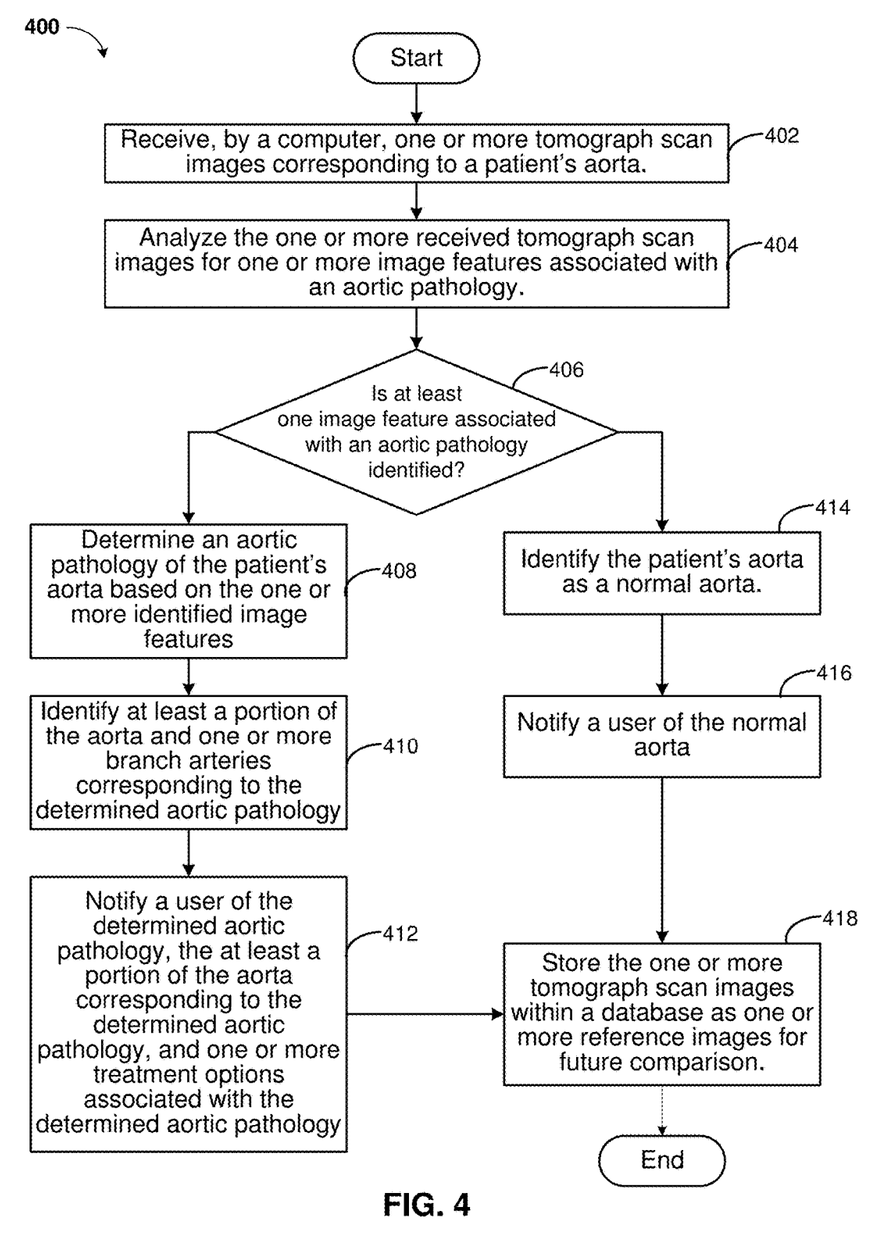
FIG. 4 is an operational flowchart illustrating the steps carried out by a program that detects and characterizes aortic pathologies, according to at least one embodiment.

Referring now to FIG. 4, an operational flowchart 400 illustrating the steps carried out by a program that detects and characterizes aortic pathologies is depicted. FIG. 4 may be described with the aid of FIGS. 1, 2, and 3A-3C. As previously described, the Aortic Pathology Characterization Program 116 (FIG. 1) may quickly and effectively diagnose aortic pathologies.

At 402, one or more tomograph scan images corresponding to a patient's aorta are received by a computer. The tomograph scan images may obtained through a variety of tomography methods, such as x-ray computed tomography (CT), positron emission tomography (PET), magnetic resonance imaging (MRI), functional magnetic resonance imaging (fMRI), or any combination of methods, such as PET-CT. According to one exemplary embodiment, the Aortic Pathology Characterization Program 116 (FIG. 1) on the server computer 114 (FIG. 1) may receive one or more tomograph scan images 300 (FIG. 2) from the computer 102 (FIG. 1) via the communication network 110 (FIG. 1). The received tomograph scan images 300 may depict any section of the aorta, such as the ascending aorta, the aortic arch, the descending aorta, and the abdominal aorta. Furthermore, the received tomograph scan images 300 may be in substantially any digital format, such as PNG, JPG, TIF, or any proprietary format.

At 404, the one or more received tomograph scan images are analyzed, by a computer, for one or more images features that may be associated with an aortic pathology. For example, the one or more received tomograph scan images may contain, among other things, one or more image features associated with an aortic pathology, such as an aortic dissection (see FIG. 3B) or aortic aneurysm (see FIG. 3C). The images may be analyzed using one or more qualitative methods, such as visual landmark detection, false lumen detection, or ridge detection. One or more stored reference images stored within a database and accessible by the computer may be used as a basis for comparison. The one or more stored reference images may contain known image features and may be used to determine the presence of the image features within the received images. Alternatively, may be one or more quantitative measurements, such as artery diameter measurements, circularity measurements, or normalization values associated with the received images. In the case of aortic dissection, the Aortic Pathology Characterization Program 116 (FIG. 1) may identify the false lumen 306 (FIG. 3B) in the tomograph scan image 300B (FIG. 3B) using visual landmark detection, ridge detection, or circularity measurements. Alternatively, in the case of aortic aneurysm, the Aortic Pathology Characterization Program 116 may identify diameter D' (FIG. 3C) in tomograph scan image 300C (FIG. 3C) as being greater than a predetermined threshold value. The predetermined threshold value may correspond generally with diameter D (FIG. 3A) associated with tomograph scan image 300A (FIG. 3A).

The aorta and possible affected regions may be localized within an image. For example the aorta and its parts (ascending, arch and descending), the subclavian artery, the renal, iliac and carotid arteries may be localized in a medical image such as CE-CT. This task may be performed with an Atlas-based segmentation method in which the current CT image may be registered in a deformable fashion to a group of previously labeled CT images (atlases). A deformable image registration may be performed in order to align a group of previously labeled CT images (atlases) to a target image for which the aorta segmentation may need to be produced. The previously labeled CTs may have labels for the anatomies of interest. After the registration, the labels from the atlases may be transformed to the coordinate system of the current image to label the intended regions and organs. Using the registration-based propagation technique, each atlas may produce one candidate segmentation for the target image. A label fusion step may then applied for integrate the multiple candidate segmentations into one consensus solution. It may be appreciated that each slice in the main image may be localized to a particular region of the aorta. The registration and label fusion processes may be used to segment the aorta for re-slicing, such that each slice may be perpendicular to the main vessel (i.e. the aorta) at a point along the vessel center line. This may be achieved by applying principal component analysis at different points along the vessel center line. In these slices, the vessel cross section may be, for example, almost circular. Thus, using this technique, the aorta may be segmented into three components: ascending aorta, aortic arch, and descending aorta.

In order to detect slices indicating, for example, a dissection, the presence of any visual landmarks that may indicate a dissection (for example a flap or irregularity in the shape of the vessel in the cross-sectional images) may be examined for each of the slices. This detection may be based on traditional image processing algorithms, such as ridge detection and circularity measures. It may also be achieved by machine learning algorithms where hand-engineered features may be produced from each cross-sectional image and may be used, for example, for classifying the image into normal and dissected slices using a machine learning approach. Alternatively, deep learning algorithms may be used to learn features directly from images. In at least one embodiment, user feedback may be fed to the system to improve detection accuracy over time. Features or images of cases misidentified as dissected or healthy by the system may be fed back to the system with correct labels from a user to increase the accuracy of the system in future.

At 406, the Aortic Pathology Characterization Program 116 (FIG. 1) determines whether at least one image feature associated with an aortic pathology is identified in the one or more tomograph scan images. If no image feature is identified, Aortic Pathology Characterization Program 116 determines the presence of a normal aorta, as will be discussed in further detail with respect to 414. If, however, at least one image feature associated with an aortic pathology is identified in the one or more tomograph scan images, the Aortic Pathology Characterization Program 116 may determine the type and extent of the aortic pathology. It may be appreciated that to increase specificity, more than one abnormal slice may need to be detected.

If at 406, the Aortic Pathology Characterization Program 116 (FIG. 1) determined that there is at least one image feature associated with an aortic pathology, the Aortic Pathology Characterization Program 116 may determine, at 408, the aortic pathology associated with the patient's aorta based on the one or more identified image features. For example, in the case of aortic dissection, the Aortic Pathology Characterization Program 116 may determine the presence of an aortic dissection in the patient's aorta based on the detection of the false lumen 306 (FIG. 3B) in tomograph scan image 300B (FIG. 3B). Alternatively, in the case of aortic aneurysm, the Aortic Pathology Characterization Program 116 may determine the presence of an aortic aneurysm based on the diameter D' (FIG. 3C) of the patient's aorta being greater than the pre-determined threshold value that may correspond to, for example, diameter D.

At 410, at least a portion of the aorta and one or more branch arteries corresponding to the determined aortic pathology are identified by the computer. The arteries affected in conjunction with the aorta may be used, among other things, to determine the type and extent of the aortic pathology. Additionally, the length of a dissection or the length and diameter of an aneurysm may also be used to determine the extent of the aortic pathology. After detection of the dissected slices, the coordinates of the centers of the vessel may be transformed from the re-sliced images to the original labeled CT image for the slices with dissection. According to these positions the type of the aorta may be decided. For example, if the center point of the first dissected slice is part of the ascending aorta or the arch before the left subclavian artery, the dissection may of Type A. Alternatively, if the center point of the first dissected slice is part of the descending aorta or arch after the left subclavian artery, the dissection may of Type B. Based on the position of the dissected slices the system can determine whether other arteries such as renal, iliac and carotid may also affected by the dissection. For example, in the case of aortic dissection, an aortic dissection affecting the ascending aorta and aortic arch—and, therefore, the brachiocephalic, left common carotid, and left subclavian arteries—may be characterized as a DeBakey Type I or Stanford Type A aortic dissection. It may be, among other things, clinically important to determine one or more affected arteries in conjunction with the aorta because the type of aortic pathology may be the deciding factor in determining treatment for the patient. For example, a Stanford Type A dissection may be treated with surgery, while a Stanford Type B dissection may be treated with medication. In operation, the Aortic Pathology Characterization Program 116 (FIG. 1) may determine, for example, that an aortic dissection occurs along the length of at least a portion of the ascending aorta 202 (FIG. 2), and the aortic arch 204 (FIG. 2). The Aortic Pathology Characterization Program 116 may also determine that the dissection affects blood flow to the brachiocephalic artery 212 (FIG. 2), the left common carotid artery 214 (FIG. 2), the left subclavian artery 216 (FIG. 2), and the renal arteries. The Aortic Pathology Characterization Program 116 may therefore characterize the aortic dissection as a Stanford Type A aortic dissection that may require surgical repair.

At 412, a user is notified by the computer of the determined aortic pathology, the at least a portion of the aorta corresponding to the determined aortic pathology and one or more treatment options associated with the determined aortic pathology. After detection and characterization of the dissection, the system may also rely on an available database of clinical knowledge to make a diagnosis and follow up recommendations based on the findings. The clinical knowledge may be acquired via mining of medical text or entered into the system by the user or a combination of both. As was previously discussed for 410, the arteries involved in the aortic pathology may aid in determining the type of aortic pathology, a recommended course of treatment, and any other next steps. This type of aortic pathology may, in turn, be important in determining the type of treatment a patient may receive. For example, Stanford Type A aortic dissections may be treated with surgery, while Stanford Type B aortic dissections may be treated with medication. According to one embodiment, the Aortic Pathology Characterization Program 116 (FIG. 1) on the server computer 114 (FIG. 1) may determine an aortic dissection affecting the ascending aorta 202 (FIG. 2), the aortic arch 204 (FIG. 2), the brachiocephalic artery 212 (FIG. 2), the left common carotid artery 214 (FIG. 2), the left subclavian artery 216 (FIG. 2) to be a Stanford Type A dissection. The Aortic Pathology Characterization Program 116 may then notify a user of software program 108 (FIG. 1) via communication network 110 (FIG. 1) that the received tomograph scan images 300 (FIG. 2) correspond to the tomograph scan images 300B (FIG. 3B) of a Stanford Type A aortic dissection. The Aortic Pathology Characterization Program 116 may further notify the user that surgical repair is the recommended treatment option. The treatment option may be determined by the Aortic Pathology Characterization Program 116 by searching the database 112 (FIG. 1) on the server computer 114 or by searching other databases 112 on other server computers 114 connected via the communication network 110. The database 112 may store clinical knowledge and other patient information that may be taken into account to propose the best treatment option for a patient. For example, surgery for Type A may be the best option if there are no contraindications identified within the stored patient data.

If at 406, there is no image feature within the tomograph scan image that may be identified as being associated with an aortic pathology, the patient's aorta may, among other things, be classified as a normal aorta by the computer. A normal aorta would not have, for example, dilation of the vessel associated with an aortic aneurysm nor one or more false lumens associated with aortic dissection. In operation, the Aortic Pathology Characterization Program 116 (FIG. 1) on the server computer 114 (FIG. 1) may identify aorta 200 (FIG. 2) as being a normal aorta based on tomograph scan image 300A (FIG. 3A) lacking any image features associated with one or more aortic pathologies.

At 416, a user is optionally notified by the computer that the patient's aorta is a normal aorta. In operation, the Aortic Pathology Characterization Program 116 (FIG. 1) on the server computer 114 (FIG. 1) may then notify a user of software program 108 (FIG. 1) via communication network 110 (FIG. 1) that the received tomograph scan images 300 (FIG. 2) correspond to the tomograph scan images 300A (FIG. 3B) of a normal aorta and that no treatment may be required at the present time.

At 418, the one or more tomograph scan images are stored by the computer within a database on the computer as one or more reference images. The one or more reference images may be used for future comparison in determining the presence of aortic pathologies, as was discussed above for 404. In operation, the Aortic Pathology Characterization Program 116 (FIG. 1) may store the one or more tomograph scan images 300 (FIG. 2) within the database 112 (FIG. 1) on the server computer 114 (FIG. 1). The one or more tomograph scan images may correspond to tomograph scan images 300A (FIG. 3A) depicting normal aortae, tomograph scan images 300B (FIG. 3B) depicting one or more aortic dissections, or tomograph scan images 300C (FIG. 3C) depicting one or more aortic aneurysms.

It may be appreciated that FIG. 4 provides only an illustration of one implementation and does not imply any limitations with regard to how different embodiments may be implemented. Many modifications to the depicted environments may be made based on design and implementation requirements. For example, as discussed above, the system disclosed herein may be used in substantially the same or similar way to detect and characterize pathologies of the heart, lungs, brain, liver, lymph nodes, and other bodily systems.

Figure 5:
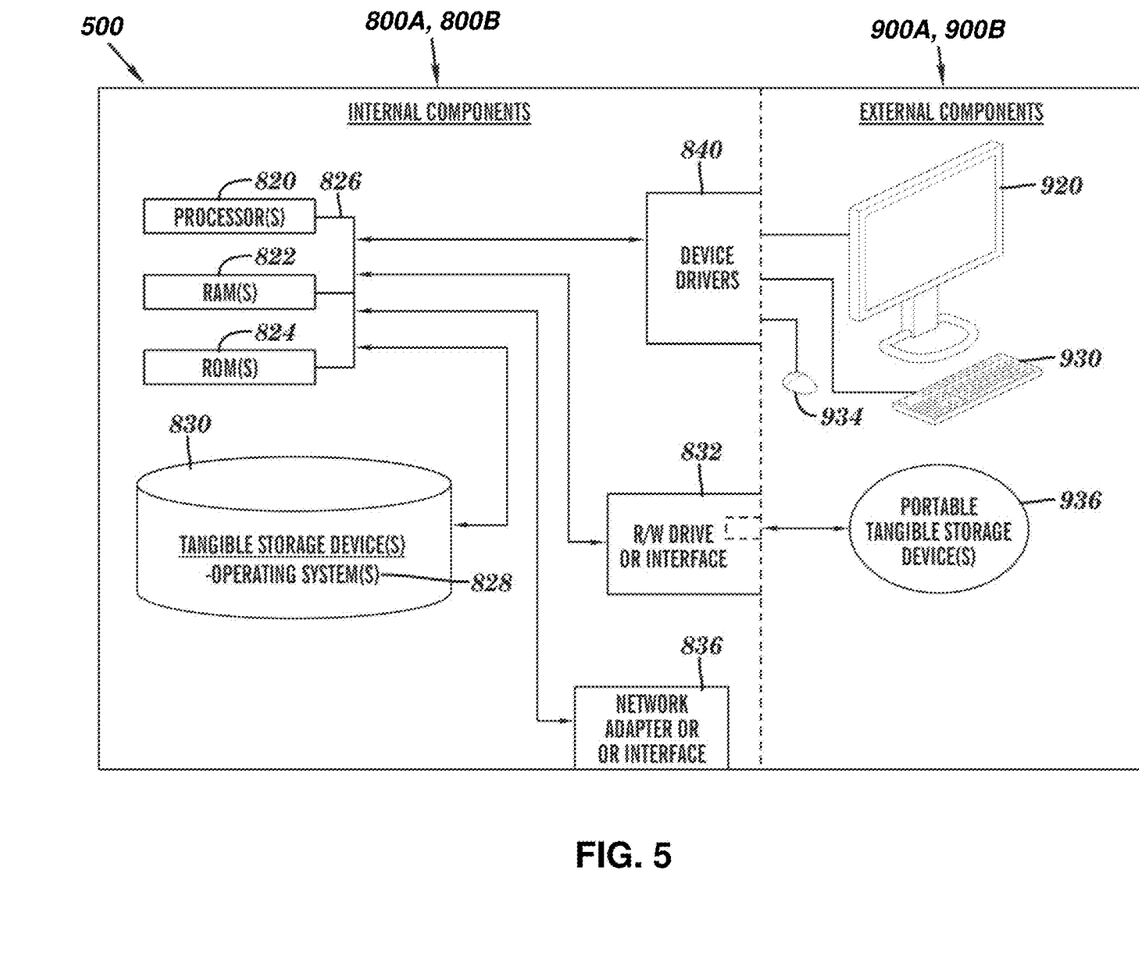
FIG. 5 is a block diagram of internal and external components of computers and servers depicted in FIG. 1 according to at least one embodiment.

FIG. 5 is a block diagram 500 of internal and external components of computers depicted in FIG. 1 in accordance with an illustrative embodiment of the present invention. It should be appreciated that FIG. 5 provides only an illustration of one implementation and does not imply any limitations with regard to the environments in which different embodiments may be implemented. Many modifications to the depicted environments may be made based on design and implementation requirements.

Computer 102 (FIG. 1) and server computer 114 (FIG. 1) may include respective sets of internal components 800A,B and external components 900A,B illustrated in FIG. 5. Each of the sets of internal components 800 include one or more processors 820, one or more computer-readable RAMs 822 and one or more computer-readable ROMs 824 on one or more buses 826, and one or more operating systems 828 and one or more computer-readable tangible storage devices 830. The one or more operating systems 828, the Software Program 108 (FIG. 1) and the Aortic Pathology Characterization Program 116 (FIG. 1) on server computer 114 (FIG. 1) are stored on one or more of the respective computer-readable tangible storage devices 830 for execution by one or more of the respective processors 820 via one or more of the respective RAMs 822 (which typically include cache memory). In the embodiment illustrated in FIG. 5, each of the computer-readable tangible storage devices 830 is a magnetic disk storage device of an internal hard drive. Alternatively, each of the computer-readable tangible storage devices 830 is a semiconductor storage device such as ROM 824, EPROM, flash memory or any other computer-readable tangible storage device that can store a computer program and digital information.

Each set of internal components 800A,B also includes a R/W drive or interface 832 to read from and write to one or more portable computer-readable tangible storage devices 936 such as a CD-ROM, DVD, memory stick, magnetic tape, magnetic disk, optical disk or semiconductor storage device. A software program, such as the Software Program 108 (FIG. 1) and the Aortic Pathology Characterization Program 116 (FIG. 1) can be stored on one or more of the respective portable computer-readable tangible storage devices 936, read via the respective R/W drive or interface 832 and loaded into the respective hard drive 830.

Each set of internal components 800A,B also includes network adapters or interfaces 836 such as a TCP/IP adapter cards; wireless Wi-Fi interface cards; or 3G, 4G, or 5G wireless interface cards or other wired or wireless communication links. The Software Program 108 (FIG. 1) and the Aortic Pathology Characterization Program 116 (FIG. 1) on the server computer 114 (FIG. 1) can be downloaded to the computer 102 (FIG. 1) and server computer 114 from an external computer via a network (for example, the Internet, a local area network or other, wide area network) and respective network adapters or interfaces 836. From the network adapters or interfaces 836, the Software Program 108 and the Aortic Pathology Characterization Program 116 on the server computer 114 are loaded into the respective hard drive 830. The network may comprise copper wires, optical fibers, wireless transmission, routers, firewalls, switches, gateway computers and/or edge servers.

Each of the sets of external components 900A,B can include a computer display monitor 920, a keyboard 930, and a computer mouse 934. External components 900A,B can also include touch screens, virtual keyboards, touch pads, pointing devices, and other human interface devices. Each of the sets of internal components 800A,B also includes device drivers 840 to interface to computer display monitor 920, keyboard 930 and computer mouse 934. The device drivers 840, R/W drive or interface 832 and network adapter or interface 836 comprise hardware and software (stored in storage device 830 and/or ROM 824).

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 6:
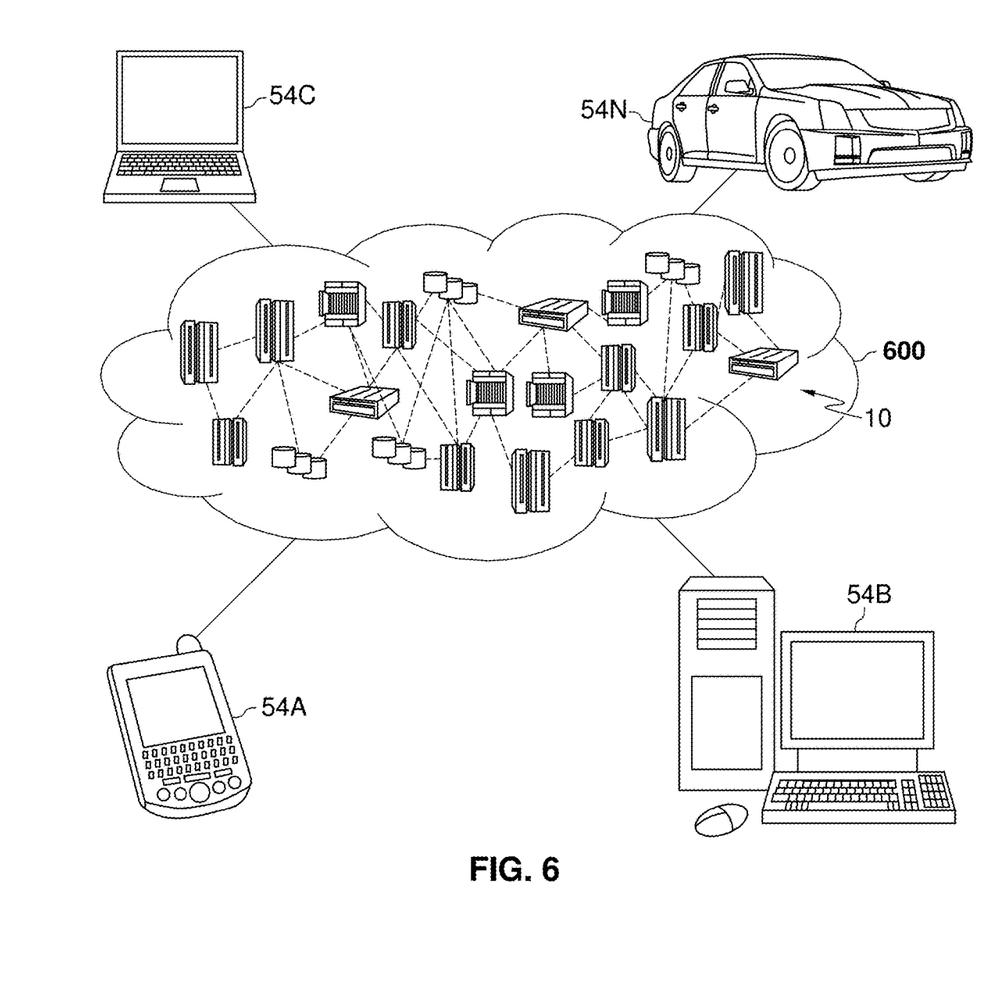
FIG. 6 is a block diagram of an illustrative cloud computing environment including the computer system depicted in FIG. 1, according to at least one embodiment.

Referring to FIG. 6, illustrative cloud computing environment 600 is depicted. As shown, cloud computing environment 600 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Cloud computing nodes 10 may communicate with one another. They may be grouped (not shown) physically or virtually, in one or more networks, such as Private, Community, Public, or Hybrid clouds as described hereinabove, or a combination thereof. This allows cloud computing environment 600 to offer infrastructure, platforms and/or software as services for which a cloud consumer does not need to maintain resources on a local computing device. It is understood that the types of computing devices 54A-N shown in FIG. 6 are intended to be illustrative only and that cloud computing nodes 10 and cloud computing environment 600 can communicate with any type of computerized device over any type of network and/or network addressable connection (e.g., using a web browser).

Figure 7:
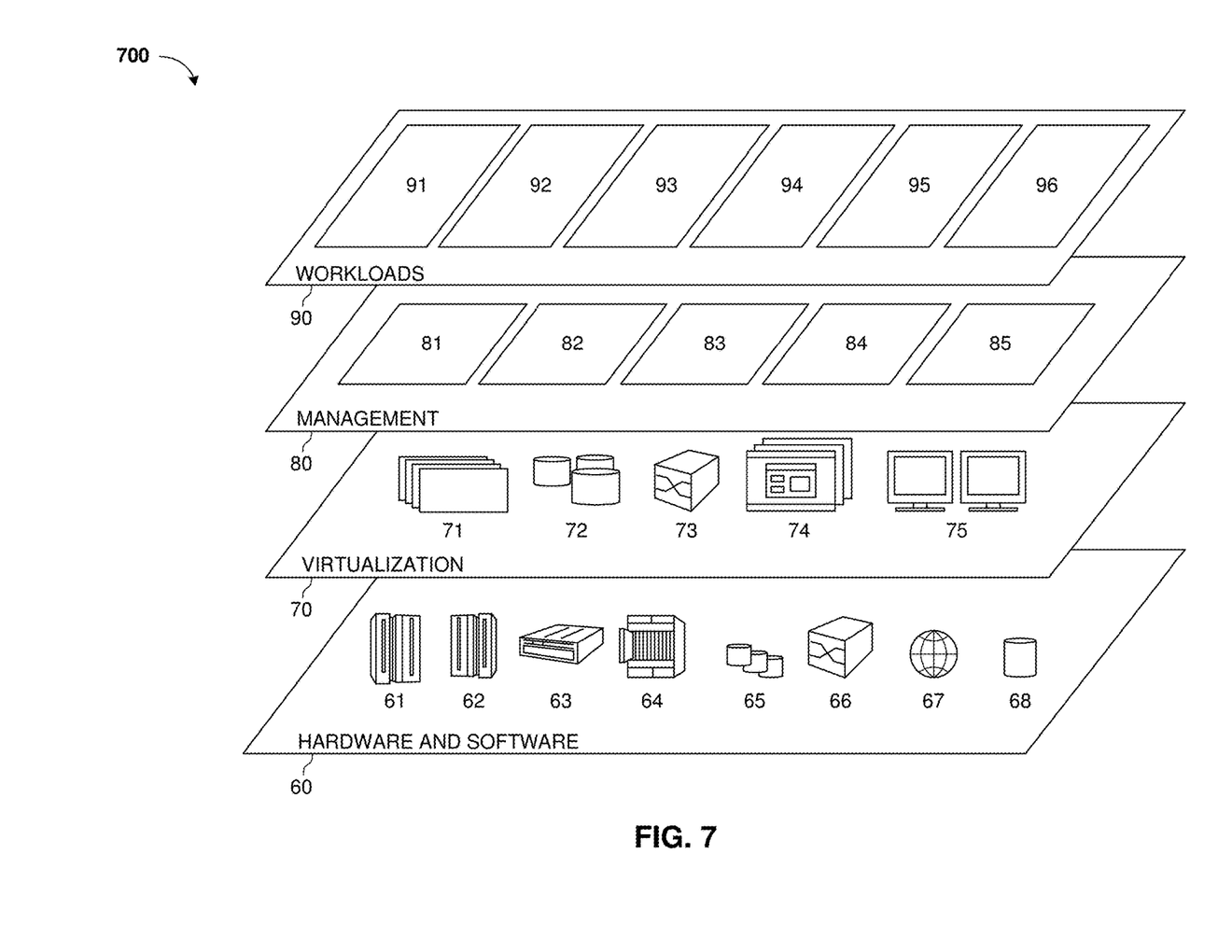
FIG. 7 is a block diagram of functional layers of the illustrative cloud computing environment of FIG. 6, according to at least one embodiment.

Referring to FIG. 7, a set of functional abstraction layers 700 provided by cloud computing environment 600 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and Aortic Pathology Characterization 96. Aortic Pathology Characterization 96 may detect and characterize one or more aortic pathologies, such as aortic dissection or an aortic aneurysm.

The present invention may be a system, a method, and/or a computer program product at any possible technical detail level of integration. The computer program product may include a computer-readable non-transitory storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for characterizing aortic pathologies, the method comprising:
    receiving, by a computer, one or more tomograph scan images corresponding to a patient's aorta;
    analyzing, by the computer, the one or more received tomograph scan images for one or more image features associated with one or more aortic pathologies;
    identifying, by the computer, one or more image features associated with the one or more aortic pathologies in the one or more analyzed tomograph scan images;
    retrieving, by the computer from a database, one or more reference images corresponding to an aortic pathology;
    determining, by the computer, an aortic pathology associated with the patient's aorta from among the one or more aortic pathologies based on the identification of the one or more image features and based on a comparison of the analyzed tomograph scan images to the one or more retrieved reference images;
    identifying, by the computer, at least a portion of the aorta and one or more branch arteries corresponding to the determined aortic pathology.

2. The method of claim 1, further comprising determining one or more treatment options in response to the determination of the aortic pathology associated with the at least a portion of the aorta and the one or more branch arteries, wherein the treatment option is based on the determined aortic pathology and clinical data associated with the patient.

3. The method of claim 2, further comprising notifying a user of at least one of:
    the determined aortic pathology,
    the at least a portion of the aorta and the one or more branch arteries corresponding to the determined aortic pathology, and
    the one or more determined treatment options.

4. The method of claim 1, further comprising storing the one or more tomograph scan images within the database as one or more reference images associated with one or more aortic pathologies.

5. The method of claim 1, wherein the aortic pathologies comprise at least one of:
    an aortic dissection,
    an abdominal aortic aneurysm, and
    a thoracic aortic aneurysm.

6. The method of claim 1, wherein the analyzing the one or more received tomograph scan images for one or more image features associated with one or more aortic pathologies comprises at least one of:
    detecting one or more visual landmarks within the one or more receiving tomograph scan images;
    detecting one or more false lumens within the one or more receiving tomograph scan images;
    detecting one or more ridges within the one or more receiving tomograph scan images;
    measuring a diameter corresponding to the patient's aorta within the one or more receiving tomograph scan images; and
    measuring a circularity value associated with the patient's aorta within the one or more receiving tomograph scan images.

7. The method of claim 1, further comprising:
    detecting a normal aorta;
    notifying a user of the detected normal aorta; and
    storing the received tomograph scan images corresponding to the detected normal aorta as one or more reference images associated with a normal aorta.

8. A computer program product for characterizing aortic pathologies, the computer program product comprising:
    one or more computer-readable non-transitory storage media and program instructions stored on the one or more computer readable non-transitory storage media, the program instructions comprising:
        program instructions to receive, by a computer, one or more tomograph scan images corresponding to a patient's aorta;
        program instructions to analyze, by the computer, the one or more received tomograph scan images for one or more image features associated with one or more aortic pathologies;
        program instructions to identify, by the computer, one or more image features associated with the one or more aortic pathologies in the one or more analyzed tomograph scan images;
        program instructions to retrieve, by the computer from a database, one or more reference images corresponding to an aortic pathology;
        program instructions to determine, by the computer, an aortic pathology associated with the patient's aorta from among the one or more aortic pathologies based on the identification of the one or more image features and based on a comparison of the analyzed tomograph scan images to the one or more retrieved reference images;
program instructions to identify, by the computer, at least a portion of the aorta and one or more branch arteries corresponding to the determined aortic pathology.

9. The computer program product of claim 8, further comprising program instructions to determine one or more treatment options in response to the determination of the aortic pathology associated with the at least a portion of the aorta and the one or more branch arteries, wherein the treatment option is based on the determined aortic pathology and clinical data associated with the patient.

10. The computer program product of claim 9, further comprising program instructions to notify a user of at least one of:
the determined aortic pathology,
the at least a portion of the aorta and the one or more branch arteries corresponding to the determined aortic pathology, and
the one or more determined treatment options.

11. The computer program product of claim 8, further comprising program instructions to store the one or more tomograph scan images within the database as one or more reference images associated with one or more aortic pathologies.

12. The computer program product of claim 8, wherein the aortic pathologies comprise at least one of:
an aortic dissection,
an abdominal aortic aneurysm, and
a thoracic aortic aneurysm.

13. The computer program product of claim 8, wherein the analyzing the one or more received tomograph scan images for one or more image features associated with one or more aortic pathologies comprises at least one of:
program instructions to detect one or more visual landmarks within the one or more receiving tomograph scan images;
program instructions to detect one or more false lumens within the one or more receiving tomograph scan images;
program instructions to detect one or more ridges within the one or more receiving tomograph scan images;
program instructions to measure a diameter corresponding to the patient's aorta within the one or more receiving tomograph scan images; and
program instructions to measure a circularity value associated with the patient's aorta within the one or more receiving tomograph scan images.

14. The computer program product of claim 8, further comprising:
program instructions to detect a normal aorta;
program instructions to notify a user of the detected normal aorta; and
program instructions to store the received tomograph scan images corresponding to the detected normal aorta as one or more reference images associated with a normal aorta.

15. A computer system for characterizing aortic pathologies, the computer system comprising:
one or more computer processors, one or more computer-readable non-transitory storage media, and program instructions stored on the one or more computer-readable non-transitory storage media for execution by at least one of the one or more computer processors, the program instructions comprising:
program instructions to receive, by a computer, one or more tomograph scan images corresponding to a patient's aorta;
program instructions to analyze, by the computer, the one or more received tomograph scan images for one or more image features associated with one or more aortic pathologies;
program instructions to identify, by the computer, one or more image features associated with the one or more aortic pathologies in the one or more analyzed tomograph scan images;
program instructions to retrieve, by the computer from a database, one or more reference images corresponding to an aortic pathology;
program instructions to determine, by the computer, an aortic pathology associated with the patient's aorta from among the one or more aortic pathologies based on the identification of the one or more image features and based on a comparison of the analyzed tomograph scan images to the one or more retrieved reference images;
program instructions to identify, by the computer, at least a portion of the aorta and one or more branch arteries corresponding to the determined aortic pathology, wherein the aortic pathologies comprise at least one of an aortic dissection, an abdominal aortic aneurysm, and a thoracic aortic aneurysm.

16. The computer system of claim 15, further comprising program instructions to determine one or more treatment options in response to the determination of the aortic pathology associated with the at least a portion of the aorta and the one or more branch arteries, wherein the treatment option is based on the determined aortic pathology and clinical data associated with the patient.

17. The computer system of claim 16, further comprising program instructions to notify a user of at least one of:
the determined aortic pathology,
the at least a portion of the aorta and the one or more branch arteries corresponding to the determined aortic pathology, and
the one or more determined treatment options.

18. The computer system of claim 15, further comprising program instructions to store the one or more tomograph scan images within the database as one or more reference images associated with one or more aortic pathologies.

19. The computer system of claim 15, wherein the analyzing the one or more received tomograph scan images for one or more image features associated with one or more aortic pathologies comprises at least one of:
program instructions to detect one or more visual landmarks within the one or more receiving tomograph scan images;
program instructions to detect one or more false lumens within the one or more receiving tomograph scan images;
program instructions to detect one or more ridges within the one or more receiving tomograph scan images;
program instructions to measure a diameter corresponding to the patient's aorta within the one or more receiving tomograph scan images; and
program instructions to measure a circularity value associated with the patient's aorta within the one or more receiving tomograph scan images.

20. The computer system of claim 15, further comprising:
program instructions to detect a normal aorta;
program instructions to notify a user of the detected normal aorta; and program instructions to store the received tomograph scan images corresponding to the detected normal aorta as one or more reference images associated with a normal aorta.

* * * * *